United States Patent [19]

Bonsignore et al.

[11] Patent Number: 5,324,849
[45] Date of Patent: Jun. 28, 1994

[54] CLASS OF PEROXY COMPOUNDS BASED ON TUNGSTEN AND DIPHOSPHONIC ACIDS AND PROCESS FOR OBTAINING THEM

[75] Inventors: Stefanio Bonsignore; Rino D'Aloisio; Paolo Soncini; Carlo Venturello, all of Novara, Italy

[73] Assignee: Enichem S.P.A., Milan, Italy

[21] Appl. No.: 995,044

[22] Filed: Dec. 22, 1992

[30] Foreign Application Priority Data

Dec. 23, 1991 [IT] Italy .................................. 003477

[51] Int. Cl.$^5$ ................................ C07F 7/22
[52] U.S. Cl. ................................ 556/14
[58] Field of Search ......................... 556/14

[56] References Cited

FOREIGN PATENT DOCUMENTS 0109273 5/1984 European Pat. Off. .

Primary Examiner—Paul J. Killos
Attorney, Agent, or Firm—Oblon, Spivak, Mcclelland, Maier & Neustadt

[57] ABSTRACT

Disclosed is a class of compounds based on tungsten and diphosphonic acids, which contain active oxygen atoms and cationic groups deriving from onium salts.

Also disclosed is the method for preparing and using said class of compounds for olefin oxidation and diol and acid oxidation reactions.

16 Claims, No Drawings

CLASS OF PEROXY COMPOUNDS BASED ON TUNGSTEN AND DIPHOSPHONIC ACIDS AND PROCESS FOR OBTAINING THEM

The present invention relates to a class of compounds based on tungsten and diphosphonic acids, which contain active oxygen atoms and cationic groups deriving from onium salts.

According to a second aspect thereof, the present invention relates to the method for preparing the above said class of compounds.

A further aspect of the present invention is using said class of compounds for oxidation reactions.

From Italian Patent Application 24 154 A/82 to the name of Montedison S.p.A., compositions of general formula:

$$Q_3XW_4O_{24-2n} \qquad (a)$$

in which:

Q stands for the cation of an onium salt;
X is a P or As atom;
n is an integer selected from 0, 1 or 2, are known.

The onium cation may also be in immobilized form on a macroporous polymeric matrix.

The above said compositions are prepared by reacting, in an acidic aqueous phase, an oxygen containing derivative of tungsten$^{VI}$, an oxygen containing phosphorus or arsenic$^{V}$ derivative and hydrogen peroxide, with an onium salt or a precursor thereof, possibly contained in an organic phase immiscible with the aqueous phase.

These compositions are used as catalysts for oxidation reactions, both in homogeneous and in heterogeneous phase, preferably according to the phase transfer technique, in the presence of hydrogen peroxide.

The present Applicant has found now that particular diphosphonic acids, combined with an oxygen-containing derivative of tungsten$^{VI}$, hydrogen peroxide and a suitable onium salt, are capable of yielding per se novel compounds.

Such compounds result to be good oxidizing agents, and furthermore may be used as additives in detergency field.

The subject-matter of the present invention is hence a class of compounds based on tungsten and particular diphosphonic acids, which contain active oxygen atoms and cationic groups deriving from onium salts.

The compounds belonging to the class of compounds according to the present invention have the general formula:

$$\{[(O_5WO)_2OP\text{-}(CXX')_n\text{-}PO(OWO_5)_2]_2WO_5\} \; Q_5 \qquad (I)$$

wherein:

n is either 1 or 2;
X and X', which may be the same or different from each other, are H or F;
Q is the cation of an onium salt constituted by quaternary salts having the formula (II):

$$(R_1,R_2,R_3,R_4M)^+ \; Y^- \qquad (II)$$

in which:

M stands for a pentavalent element belonging to Group VA of the Periodic System of Elements, such as N, P, As, Sb;

Y- is a stable inorganic anion, such as Cl-, HSO$_4$-, NO$_3$-, and so forth;
R$^1$, R$^2$, R$^3$, R$^4$, which may be the same, or different from each other, represent H or alkyl radicals, wherein at least one of said radicals may also be linked to a polymeric matrix of either organic or inorganic type.

When R moieties are alkyl radicals, they can be selected from univalent hydrocarbyl radicals containing a total number of carbon atoms of up to 70, and preferably comprised within the range of from 25 to 40.

The compounds falling within the scope of the above mentioned formula (I) are synthetized by causing an acidic aqueous phase (pH<1) containing the diphosphonic acid, a suitable oxygen-containing tungsten$^{VI}$ compound and hydrogen peroxide, to react with an organic media substantially immiscible with water, containing an onium salt, according to preestablished—although not critical—molar ratios, under substantially room conditions of pressure and at temperatures preferably comprised within the range of from 20° to 80° C.

Diphosphonic acids which may be used are methylenediphosphonic acid [Formula (I) wherein n=1 and X=X'=H] and ethylenediphosphonic acid [Formula (I) wherein n=2 and X=X'=H].

In the preparation of the compounds of formula (I), as tungsten derivatives, preferably oxygen-containing derivatives of tungsten$^{VI}$ are used, such as tungstic acid or its alcali metal salts.

However, in general, any tungsten derivatives, or tungsten itself, may be used, provided that, under the conditions provided for the reaction, said tungsten derivative, or metal tungsten, may originate in situ said oxygen containing derivative of tungsten$^{VI}$, as specified hereinabove.

Therefore, for example, WO$_2$, W$_2$O$_5$, WO$_3$, WS$_2$, WS$_3$, tungsten oxychloride, tungsten chloride and tungsten hexacarbonyl, may be used.

The onium salts are constituted by quaternary compounds of general formula (II), as already defined above.

According to whether M is an N, P, As, Sb atom, the corresponding onium salts are obtained, i.e., ammonium (N) salts, phosphonium (P) salts, arsonium (As) salts, stibonium (Sb) salts; methyl trioctyl ammonium chloride, dimethyl [dihexadecyl (24%)+dioctadecyl (76%)] ammonium chloride (Arquad 2HT), tetraalkylammonium chloride, tetraalkylphosphonium chloride, trialkylammonium chloride and trialkylphosphonium hydrogensulfate are preferred.

Furthermore, as the source for onium salt, onium salts, preferably onium chlorides, may be used, which are immobilized on polymeric macroporous matrices of organic type (polystyrene type) or of inorganic type (based on silica, alumina, titanium-silicalite, and so on), which can be prepared according to techniques known from the prior art, or are available from the market.

In this case, products are obtained which are insoluble in aqueous and organic solvents, and hence are suitable for those reactions in which the compounds of formula (I) are used as phase transfer catalysts, according to the triple-phase (aqueous phase—organic phase—solid phase) technique.

The supported compounds are particularly interesting, because they supply the possibility of recovering the catalyst, which has now been made insoluble both in water and in common organic solvents.

As the organic solvents for the onium salt, inert solvents are generally used which are substantially immiscible with the aqueous phase containing the tungsten compound and phosponic acid, and are capable of dissolving the catalyst which is the reaction product.

Aromatic hydrocarbons, such as benzene, toluene, several xylenes, and so forth; chlorohydrocarbons, such as dichloromethane, dichloroethane, trichloroethane, chlorobenzene, and so forth, and their mixtures, have proven to be particularly suitable.

As regards the molar ratios of the reactants, their values are never critical for the purposes of the formation of the compounds (I); however, the following values represent, as to said ratios, the operating values which secured advantageous results from the viewpoints of yield and product purity.

Therefore, per each mol of diphosphonic acid, at least 4.5 mols of tungsten compound and up to 2 mols of onium salt are used.

These are optimal values; in any case, the use of larger amounts of tungsten compounds does not yield any advantages, and larger amounts of onium salts imply a gradual purity decrease.

As regards $H_2O_2$, from 2.5 to 6 mols per each mol of tungsten$^{VI}$ compound suffice. Larger amounts are compatible.

When compounds of less than-hexavalent tungsten are used, to the above said amount of $H_2O_2$, that amount should be added which is necessary in order to bring tungsten to its oxidation state of tungsten$^{VI}$.

The concentration of the reactants, in the aqueous phase as well as in the organic phase, does not represent a critical parameter; the same holds true for the reaction times.

The products of formula (I) obtained according to the present invention are in the physical states of solids, or oily, thick liquids.

They are generally soluble in aromatic hydrocarbons and chlorohydrocarbons; on the contrary, they are poorly soluble, or insoluble, in water, as a direct function of the number of carbon atoms and/or of the nature of the radicals $R_1$, $R_2$, $R_3$ and $R_4$ and of the onium salt used.

The compounds (I) obtained in that way display interesting applications; thanks to active oxygen present in them, they may hence find use as oxidizer agents in general and, in particular, e.g., in the reactions of epoxidation of olefinic compounds, for which they showed a high epoxidating activity.

Thanks to their characteristics of good solubility in the usual organic solvents and of negligible solubility in water, the compounds of formula (I) are suitable for use as (ep)oxidation catalysts according to the phase transfer technique, using hydrogen peroxide as the primary oxidizer agent.

The use of the compounds of formula (I) according to the phase transfer technique, makes it possible very diluted hydrogen peroxide to be used, even at a lower concentration than 10%, with a high conversion of same $H_2O_2$ being obtained simultaneously, associated with a high selectivity to the epoxide of the olefin, with no need—as it occurs, on the contrary, with other types of processes—for the system having to be homogenized with the use of suitable solvents and, above all, without having to resort to any burdensome operations of water removal from reaction environment.

For merely exemplifying purposes, in greater detail, a possible route for preparing the compounds of formula (I) may be as follows: an aqueous solution of the oxygen containing derivative of tungsten$^{VI}$ (e.g., tungstic acid) and of diphosphonic acid, in the preselected molar ratios, is treated, with stirring, with an aqueous solution of $H_2O_2$ in the desired ratio, at a temperature comprised within the approximate range of from 20° C. to 80° C.

Then, still with stirring, the amount is added, preferably at room temperature, of the selected onium salt dissolved in an organic, water-immiscible, solvent, e.g., dichloroethane or benzene.

The resulting two-phase mixture is stirred for a further 15–30 minutes.

Then the organic phase is separated and is evaporated under vacuum at 40°–30° C., the desired product being obtained as a solid, or a thick liquid substance.

In the case of compounds supported on matrices, they are obtained by treating, in the aqueous phase, the tungsten compound (tungstic acid) and the suitable diphosphonic acid, with $H_2O_2$, as already disclosed hereinabove.

Then, the organic solvent and the onium salt supported on the polymeric carrier are added and the resulting mixture is kept stirred 2 hours at 80° C.

The solid product is then separated by filtering.

The characteristics which characterize the products of formula (I) make it possible them to be used as catalysts in reactions of olefin (ep)oxidation with diluted $H_2O_2$, by means of the phase transfer technique.

Schematically summarized, the phase transfer technique used for the compounds in question consists of carrying out the reaction in a double-phase system (immiscible liquids), in particular in an aqueous liquid/organic liquid system, essentially constituted by:

an organic phase containing the compound of formula (I), the olefin to be (ep)oxidated and the possible solvent;

an aqueous phase, containing hydrogen peroxide.

However, the supported compound may constitute a third, solid, phase.

The reaction of olefin (ep)oxidation with the use of the catalysts (I) according to the present invention is preferably carried out under the following operating conditions: as said hereinabove, it is preferably carried out in a binary aqueous/organic system, with strong stirring, in the presence of the catalyst (I).

The organic phase is constituted by the organic substrate (e.g., the olefin), and a possible organic solvent, and the hydrogen peroxide containing aqueous phase.

When the catalyst supported on a matrix is used, the reaction is carried out under the same operating conditions, but in the presence of an aqueous/organic liquid/solid three-phase system.

The operating temperature and pressure are determined by the reactivity and nature of the substrate, by the stability of hydrogen peroxide, and by the catalyst used.

Temperatures comprised within the range of from 0° C. to 120° C. and pressures ranging from room pressure up to 100 atm should be regarded as sufficient from the operating viewpoint.

In the case that the substrate is constituted by olefins, these can be represented by the following formula:

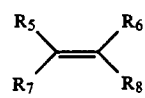

in which $R_5$, $R_6$, $R_7$ and $R_8$, which may also be substituted with functional groups inert under the reaction conditions, indifferently represent hydrogen atoms or hydrocarbyl moieties, such as alkyl and alkenyl radicals of up to 30 carbon atoms, cycloalkyl and cycloalkenyl radicals of from 3 to 12 carbon atoms, which may also be branched, aryl, alkylaryl, alkenylaryl radicals of from 6 to 12 carbon atoms; and, furthermore, one of $R_5$, $R_6$, $R_7$ and $R_8$ radicals, taken jointly with an adjacent group, may represent alkyl or alkenyl radicals or up to 12 carbon atoms in the resulting ring structure.

Substituent groups inert under the reaction conditions are, e.g., the hydroxy radicals, halogens (Cl, Br, F, I), nitro, alkoxy, amino, carbonyl, carboxy, ester, amido, nitrilo groups, and so forth.

As said above, the radicals $R_5$, $R_6$, $R_7$ and $R_8$ may also be alkenyls; in other terms, the process according to the present invention may also be applied to polyunsaturated olefins; such as dienes, trienes, which may be conjugated, or less.

The reaction time depends on the nature of the catalyst and on the type of solvent and olefin used; in general, times comprised within the range of from a few minutes, up to some hours, are enough in order to complete the reaction.

The catalyst is used in amounts comprised within the range of from 0.0001 to 1 g-atom of metal, approximately per each mol of hydrogen peroxide, and preferably of from 0,005 to 0,05 g-atom approximately per each mol of hydrogen peroxide. As said hereinabove, the reaction is carried out under phase transfer conditions, e.g., in a double-phase aqueous liquid/organic liquid system.

In particular, the organic phase may indifferently be constituted by the same olefin used as the reactant, used in a suitable excess thereof, or it may be constituted by the reactant olefin dissolved in true organic solvents substantially immiscible with the aqueous phase.

The selection of the type of organic phase will be clear for those skilled in the art according to the reactivity of the olefin used as the starting material, and to the processing parameters used.

When in the organic phase inert solvents immiscible with water are used, the concentration of the olefin in the solvent is not critical for the purposes of process operations.

Operating values for olefin concentration in the organic phase are comprised within the approximate range of from 5% to 95% by weight; higher or lower values are compatible within their feasibility limits.

Hydrogen peroxide concentration in the aqueous phase should suitably be kept comprised within the approximate range of from 0.1 to 70%.

The present invention is disclosed in the following in greater detail on the basis of the following examples supplied for merely illustrative, non-limitative purposes.

EXAMPLE 1

2.50 g of $H_2WHO_2$ (10 mmol) and 7 mL of $H_2O_2$ at 30% w/v (weight/volume) (about 62 mmol) are charged to a beaker.

The suspension of tungstic acid is kept at about 60° C., with stirring, until tungstic acid is completely dissolved.

After cooling, 0.39 g of methylenediphosphonic acid $CH_2$-$[PO(OH)_2]_2$ (2.20 mmol) is added to the resulting colourless solution.

The solution obtained in that way is diluted with $H_2O$ to a total volume of 30 mL, is filtered, and is charged to a reaction vessel equipped with dripping funnel and stirring means and, with stirring, 1.60 g of methyl-trioctyl-ammonium chloride (3.96 mmol) dissolved in 40 mL of methylene chloride is added dropwise during approximately 2 minutes.

After a further 15-minute stirring, the organic phase is separated and is evaporated under vacuum at 40°–50° C.

2.71 g is obtained (97% relatively to onium salt used) of a thick, colourless oil.

Elemental analysis: Calculated for $C_{202}H_{436}N_8P_4W_9O_{57}$: C: 42.80; H: 7.75; N: 1.98; P: 2.19; W: 29.19; Found: C: 42.92; H: 7.83; N: 2.01; P: 2.03; W: 29.2;

Active oxygen found: 5.10%;

$^{31}P$ NMR ($CDCl_3$, 85% $H_3PO_4$ as external reference): Delta: +28.2 (broadened td), +17.1 (td, $J_1 = 19.7$ Hz, $J_2 = 7.3$ Hz);

I.R. (KBr): 3035, 2955, 2925, 1711, 1485, 1467, 1378, 1189, 1119, 1061, 1002, 972, 895, 855, 845, 815, 761, 724, 650, 589, 577, 540, 519, 502, 434 cm$^{-1}$.

EXAMPLE 2

The process is carried out as in Example 1, with methylenediphosphonic acid being replaced by 0.42 g of ethylenediphosphonic acid (2.20 mmol).

2.70 g (96%) of product is obtained as a thick, colourless oil.

Elemental analysis: Calculated for $C_{204}H_{440}N_6P_4W_9O_{57}$: C: 43.01; H: 7.79; N: 1.97; P: 2.18; W: 29.05; Found: C: 42.48; H: 7.89; N: 1.94; P: 2.08; W: 28.9;

Active oxygen found: 5.15%;

I.R. (KBr): 3035, 2956, 2921, 2857, 1713, 1485, 1467, 1379, 1202, 1165, 1119, 1087, 996, 961, 890, 856, 845, 768, 724, 646, 587, 574, 550, 515, 447 cm$^{-1}$.

EXAMPLE 3

5.1 ml of $H_2O_2$ at 40% w/v (weight/volume) (60 mmol), 0.84 g of the compound of Example 1 (equivalent to 1.34 mmol of tungsten) dissolved in 10 ml of 1,2-dichloroethane and 11.5 g of 1-octene (100 mmol) are charged to a 4-neck reaction vessel of 250 ml, equipped with blade stirrer, thermometer and reflux condenser.

With strong stirring, the mixture is rapidly heated up to 70° C. and is kept 45 minutes at that temperature.

At the end of the heating period, by iodometric way 0.6 mmol of unreacted $H_2O_2$, and by gas-chromatography 56.4 mmol of 1,2-epoxyoctane are detected in the aqueous phase and in the organic phase respectively. These values correspond to a hydrogen peroxide conversion of 99%, with a selectivity to epoxide, relatively to reacted hydrogen peroxide, of 95%.

EXAMPLE 4

Example 3 is repeated using 12.7 ml of $H_2O_2$ at 16% w/v (60 mmol) instead of 40% $H_2O_2$.

At the end of the reaction, the analyses demonstrate the presence of 3.0 mmol of unreacted $H_2O_2$ (conversion: 95%) and 53 mmol of 1,2-epoxyoctane (selectivity 93%, as referred to reacted $H_2O_2$).

EXAMPLE 5

Example 4 is repeated, with the reaction mixture being kept stirred at 70° C. for 30 minutes, instead of 45 minutes.

At the end of the reaction, the analyses demonstrate the presence of 3.2 mmol of unreacted $H_2O_2$ (conversion: 95%) and 52 mmol of 1,2-epoxyoctane (selectivity 92%, as referred to reacted $H_2O_2$).

EXAMPLE 6

Example 3 is repeated, using 18.3 g of 1-dodecene (100 mmol) instead of 1-octene, and with the reaction mixture being stirred for 60 minutes at 70° C.

At the end of the reaction, the analyses demonstrate the presence of 1.96 mmol of unreacted $H_2O_2$ (conversion: 97%) and 54 mmol of 1,2-epoxydodecane (selectivity 93%, as referred to reacted $H_2O_2$).

EXAMPLE 7

Example 3 is repeated, using 11.7 g of allyl chloride (153 mmol) instead of 1-octene, and with the reaction mixture being kept stirred 150 minutes at 55° C.

At the end of the reaction, the analyses demonstrate the presence of 10.5 mmol of unreacted $H_2O_2$ (conversion: 82.5%) and 43 mmol of epichlorohydrin (selectivity 87%, as referred to reacted $H_2O_2$).

EXAMPLE 8

Example 3 is repeated, using 11.22 g of 4-octene (100 mmol) instead of 1-octene.

At the end of the reaction, the analyses demonstrate the presence of 0.1 mmol of unreacted $H_2O_2$ (conversion: 99%) and 58.7 mmol of 3,4-epoxyoctane (selectivity 98%, as referred to reacted $H_2O_2$).

EXAMPLE 9

Example 3 is repeated, using 0.85 g (equivalent to 1.34 mmol of tungsten) of compound of Example 2 in lieu of the compound of Example 1.

At the end of the reaction, the analyses demonstrate the presence of 1.8 mol of unreacted $H_2O_2$ (conversion: 97%) and 54 mmol of 1,2-epoxyoctane (selectivity 93%, as referred to reacted $H_2O_2$).

EXAMPLE 10

Example 4 is repeated, using 0.85 g (equivalent to 1.34 mmol of tungsten) of compound of Example 2 in lieu of the compound of Example 1.

At the end of the reaction, the analyses demonstrate the presence of 20.4 mmol of unreacted $H_2O_2$ (conversion: 66%) and 53.9 mmol of 1,2-epoxyoctane (selectivity 90%, as referred to reacted $H_2O_2$).

EXAMPLE 11

8.76 ml of $H_2O_2$ at 40% w/v (weight/volume) (103 mmol), 0.84 g of the compound of Example 1 (equivalent to 1.34 mmol of tungsten) and 6.0 g of oleic acid (20.6 mmol) are charged to a 4-neck reaction vessel of 250 ml, equipped with blade stirrer, thermometer and reflux condenser.

With strong stirring, the mixture is rapidly heated up to 60° C. and is kept 7 hours at that temperature.

At the end of the heating period, the reaction products are extracted from the mixture with ethyl ether.

In the aqueous phase, by iodometric way, 1 mmol of unreacted $H_2O_2$ (conversion 98%), and in the organic phase, by chromatography 16.76 mmol of pelargonic acid (yield, referred to the amount of oleic acid: 81%) and 16.44 mmol of azelaic acid (yield: 79.71%) are detected.

EXAMPLE 12

13.76 ml of $H_2O_2$ at 40% w/v (weight/volume) (165 mmol), 0.84 g of the compound of Example 1 (equivalent to 1.34 mmol of tungsten) dissolved in 10 ml of 1,2-dichloroethane and 7.12 g (50 mmol) of phenylethyleneglycol are charged to a 4-neck reaction vessel of 250 ml, equipped with blade stirrer, thermometer and reflux condenser.

With strong stirring, the mixture is rapidly heated up to 75° C. and is kept 5 hours at that temperature.

At the end, the reaction mixture is diluted with water and its pH value is approximately adjusted at 8 by means of the addition of a 1N solution of NaOH.

The aqueous phase is separated and then is acidified with concentrated HCl.

An extraction with ethyl ether is then carried out; from the organic phase, separated and subsequently evaporated, 5.45 g of benzoic acid is weighed (yield, as referred to the amount of phenyl ethylene glycol: 89%).

We claim:

1. Compounds based on tungsten and diphosphonic acids, containing active oxygen atoms and cationic groups deriving from onium salts, having the general formula:

$$\{[(O_5WO)_2OP\text{-}(CXX')_n\text{-}PO(OWO_5)_2]_2WO_5\}\ Q_5 \qquad (I)$$

wherein:

n is either 1 or 2;

X and X', which may be the same or different from each other, are H or F;

Q is the cation of an onium salt constituted by quaternary salts having the formula (II):

$$(R_1,R_2,R_3,R_4\ M)^+\ Y^- \qquad (II)$$

in which:

M stands for a pentavalent element belonging to Group VA of the Periodic System of Elements;

$Y^-$ is a stable inorganic anion;

$R^1$, $R^2$, $R^3$, $R^4$, which may be the same, or different from each other, represent H or alkyl radicals.

2. Compounds according to claim 1, characterized in that, when said R moieties are alkyl radicals, they can be selected from univalent hydrocarbyl radicals containing a total number of carbon atoms of up to 70.

3. Compounds according to claim 2, characterized in that said alkyl radicals R preferably contain a total number of carbon atoms comprised within the range of from 25 to 40.

4. Compounds according to claim 1, characterized in that at least one of said radicals is linked to a polymeric macroporous matrix of either organic or inorganic type.

5. Compounds according to claim 4, characterized in that said polymeric macroporous matrix of organic type is of polystyrene nature.

6. Compounds according to claim 4, characterized in that said polymeric macroporous matrix of inorganic type is based on silica, alumina or titanium-silicalite.

7. Compounds according to claim 1, characterized in that said pentavalent elements belonging to the Group VA of the Periodic System of Elements are selected from N, P, As, Sb.

8. Compounds according to claim 1, characterized in that said inorganic anion is selected from Cl-, $HSO_4$- and $NO_3$-.

9. Compounds according to claim 1, characterized in that Q is the cation of an onium salt constituted by quaternary salts selected from among methyl trioctyl ammonium chloride, dimethyl [dihexadecyl (24%)+dioctadecyl (76%)] ammonium chloride (Arquad 2HT), tetraalkylammonium chloride, tetraalkylphosphonium chloride, trialkylammonium chloride and trialkylphosphonium hydrogensulfate.

10. Process for obtaining the compounds of formula (I) according to claim 1, characterized in that an acidic aqueous phase (pH<1) containing the diphosphonic acid, the oxygen-containing tungsten$^{VI}$ compound and hydrogen peroxide is reacted with an organic phase substantially immiscible with water, containing a free or immobilized onium salt.

11. Process for obtaining the compounds of formula (I), according to claim 10, characterized in that, as tungsten derivatives, tungstic acid or its alkali metal salts or other tungsten compounds which, under the reaction conditions, are capable of generating tungstic acid are used.

12. Process for obtaining the compounds of formula (I), according to claim 10, characterized in that the diphosphonic acids used are methylenediphosphonic acid or ethylenediphosphonic acid.

13. Process for obtaining the compounds of formula (I), according to claim 10, characterized in that, the solvents used in order to dissolve onium salts are selected from aromatic hydrocarbons, chlorohydrocarbons, and their mixtures.

14. Process for obtaining the compounds of formula (I), according to claim 11, wherein said other tungsten compounds are selected from the group consisting of $WO_2$, $W_2O_5$, $WO_3$, $WS_2$, $WS_3$, tungsten oxychloride, tungsten chloride, tungsten hexocarbonyl and a mixture thereof.

15. Process for obtaining compounds of formula (I), according to claim 13, wherein said solvents are selected from the group consisting of benzene, toluene, several xylenes, dichloromethane, dichloroethane, trichloroethane, dichlorobenzene, and a mixture thereof.

16. Process for obtaining compounds of formula (I) according to claim 10, wherein said diphosphonic acid, said oxygen-containing tungsten$^{VI}$ compound and said hydrogen peroxide are reacted under atmospheric pressure and at temperatures comprised within the range of from 20° to 80° C.

* * * * *